United States Patent [19]

Cordle et al.

[11] Patent Number: 4,897,465

[45] Date of Patent: Jan. 30, 1990

[54] ENRICHMENT AND CONCENTRATION OF PROTEINS BY ULTRAFILTRATION

[75] Inventors: Christopher T. Cordle, Centerburg; Larry G. Criswell, Columbus, both of Ohio; Ronald L. Thomas, Clemson, S.C.

[73] Assignee: Abbott Laboratories, Abbott Park, Ill.

[21] Appl. No.: 256,813

[22] Filed: Oct. 12, 1988

[51] Int. Cl.$^4$ .................... C07K 3/26; C07K 15/14; B07C 5/18

[52] U.S. Cl. .................... 530/387; 530/414; 530/412; 210/650

[58] Field of Search .................... 530/412, 414, 387; 210/650

[56] References Cited

U.S. PATENT DOCUMENTS

| | | | |
|---|---|---|---|
| 3,431,201 | 3/1969 | Johnson et al. | 210/23 |
| 3,977,967 | 8/1976 | Trulsen et al. | 210/638 |
| 4,485,040 | 11/1984 | Roger et al. | 530/366 |
| 4,644,056 | 2/1987 | Kothe et al. | 530/387 |

*Primary Examiner*—Margaret Moskowitz
*Assistant Examiner*—Keith C. Furman
*Attorney, Agent, or Firm*—Donald O. Nickey; Edward H. Gorman

[57] ABSTRACT

Disclosed are ultrafiltration processes for the enrichment and concentration of selected proteins from protein conaining fluids. Illustratively, IgG is concentrated from whey by means of multiple ultrafiltration "passes", using a metallic oxide ultrafiltration membrane, which are characterized by differing pH's.

40 Claims, 5 Drawing Sheets

ENRICHMENT AND CONCENTRATION OF PROTEINS BY ULTRAFILTRATION

BACKGROUND OF THE INVENTION

1. Field of the Invention

The present invention relates generally to improved processes for concentrating desired proteins from fluids and more particularly, to processes for obtaining immunoglobulins from fluids by ultrafiltration through metallic membranes.

2. Background

Filtration is a much used technique for separating wanted substances from those which are unwanted. There are two customary ways in which a feed stream meets a filter: dead-end filtration and cross flow filtration. In dead-end filtration, the feed stream flows perpendicular to the filter surface. In cross flow filtration, on the other hand, the feed stream runs parallel to the filter and the filtrate diffuses across it. The filters used during filtration are often classified by retained particle size. For example, membrane microfilters generally retain particles 0.1–10 microns in diameter, ultrafilters generally retain particles and macromolecules of 1,000–500,000 daltons (approximately 0.001–0.02 microns in diameter), and hyperfilters generally retain molecules of 200–300 daltons. In the laboratory, filter selection is usually straight forward, but scale-up to industrial applications often presents numerous difficulties.

In theory, ultrafiltration should permit the selective separation, concentration, and purification of protein components. The product which passes through the membrane is known as the ultrafiltrate or "permeate" and the product which is retained and concentrated is known as the "retentate".

In practice, ultrafiltration does not proceed according to ideal hypotheses. For example, during ultrafiltration of whey, the retentate has a relatively great residual content of fat, bacteria, and mineral elements which complicate the ideal ultrafiltration process. In addition, most current ultrafiltration membranes have variable pore diameters. Their cut-off capacity is not absolutely accurate and does not correspond to an ideal isoporous membrane. Furthermore, the permeate flux (volume of product per unit of filter area per unit of time) of an ultrafiltration membrane is greatly affected by the presence of a polarization layer or by fouling of the membrane.

Polarization layers form in the course of ultrafiltration and modify the transfer of solutes across the membrane, thereby lowering the permeation rate of the apparatus and changing its separation characteristics. Polarization is caused by convection through the membrane. If fluid flows through the membrane faster than the retained material can diffuse back into the bulk fluid, a saturated layer builds up next to the membrane. The layer's depth and its resistance to flow depend on the speed at which the retentate is circulated. The total permeability of the membrane in the course of operation depends on the polarization layer's thickness and also the nature of its components. The resistance due to fouling builds as deposits chemically bind to the membrane. Fouling is quite distinct from polarization, in which the interfering layer is held against the membrane by hydrodynamic (not chemical) forces.

To obtain highly purified concentrates, filtration may be followed or accompanied by diafiltration which consists of washing the protein concentrates and subjecting them to another filtration. For example, during diafiltration a protein concentrate is brought into contact with the ultrafiltration membrane at the same time as the washing solution, e.g., an aqueous solution. Diafiltration reduces the filterable components from the retentate. It may be a batch process (dilutions followed by successive concentrations) or a continuous process (water is added at the same rate as the permeate is eliminated). In general, protein concentrates of enhanced purity may be obtained by diafiltration.

Roger et al., U.S. Pat. No. 4,485,040 relates to a process of obtaining an alpha-lactalbumin enriched product from whey. The disclosed process carries out a first ultrafiltration on unpasteurized raw whey with membranes having a molecular weight cut-off greater than 5,000 Daltons at a pH between 6.3 and 7 and a temperature between 30° C. and 60° C. to retain the whey proteins. The permeate then undergoes a second ultrafiltration (which is preferably diafiltration) with a membrane capable of retaining alpha-lactalbumin, preferably having a cut-off less than 5,000 Daltons, and recovering the retentate of the second ultrafiltration which constitutes the alpha-lactalbumin enriched product sought. Such a process is reported to fractionate alpha-lactalbumin from whey, but it reportedly does so by means of easily-fouled hollow fiber membranes without use of a pH shift.

Kothe et al., U.S. Pat. No. 4,644,056 relates to a method of preparing a solution of lactic or colostric immunoglobulins or both. In the disclosed method, milk or colostrum is acidified to a pH of 4.0–5.5, the fluid is diluted, and the diluted, acidified fluid is subjected to cross-flow diafiltration in a filtration unit with a mean pore size of 0.1–1.2 micrometers. The volume of the fluid is kept constant throughout this initial filtration by adding sodium-chloride solution. This initial diafiltration retains casein, and the permeate is a clear solution that contains all the whey proteins and low molecular weight components. The low molecular weight components are then removed from the first permeate by means of a second cross-flow diafiltration in a filtration unit with a mean pore size of 5,000–80,000 daltons, preferably 10,000 daltons. The pH of the fluid for this second filtration is kept between 4.0–5.5. The retentate of the second cross-flow diafiltration constitutes the immunoglobulin product sought. In such a process, immunoglobulins are reported to be harvested from colostrum or hyperimmunized milk, but this result is reported to be achieved by means of easily fouled hollow fiber membranes and the immunoglobulins were not enriched compared to the other protein species. An attempt is made to overcome the handicap of hollow fiber membranes by extensive use of diafiltration which renders this process not practical for large industrial applications.

Japanese patent publication 60-248152 relates to a method of manufacturing calcium fortified salts and their use. In the disclosed method, concentrated, acidified (pH adjusted to 5.0 or below) cheese whey is filtered through such membranes as an ultrafiltration membrane and an electrodialytic membrane to allow calcium to come out through the membrane in its ionic state in solution with phosphate and citrate ions. The filtrate thus obtained is adjusted to pH 6.0–9.0 by the addition of alkaline solution so as to obtain a precipitate of calcium phosphate and calcium citrate which is isolated by centrifugation. This patent does not disclose a means by which an enrichment and concentration of proteins in a fluid can be obtained.

Thomas et al., U.S. Pat. No. 4,716,044 relates to an improved process for obtaining juice from fruit. The disclosed process subjects a fluid puree of fruit and juice to a single ultrafiltration through a rigid porous tubular housing which has a food grade ultrafiltration membrane, preferably a metallic oxide membrane, deposited on its inside surfaces. During the single pass, water soluble sugars, organic acids, flavor compounds and the like reportedly pass through the disclosed membrane while insoluble solids, proteins of molecular weight greater than about 14,000, and all microorganisms reportedly are retained in the fruit retentate. Although this patent does disclose a means by which a concentration of proteins in a fluid occurs, it does not contemplate enriching a specific protein fraction of a fluid by means of ultrafiltration and a pH shift.

Trulson et al., U.S. Pat. No. 3,977,967 relates to an ultrafiltration apparatus to be used for the concentration and separaton of components contained in liquids. The disclosed apparatus is reportedly comprised of a module which contains a plurality of axially aligned, hollow tubular members which have a defined porosity and a substantially uniform, continuous, adherent, porous coating of preformed, aggregated, inorganic metal oxide particles on their interior or exterior surface. In the disclosed process, low molecular weight dissolved phases reportedly permeate the walls of the tubes while the larger diameter molecules are retained in the liquid. In a preferred embodiment of the disclosure, the metal oxide coated onto the ultrafiltration apparatus is zirconia. Trulson et al. report that this ultrafiltration apparatus can be used to concentrate and separate the protein fraction of cottage cheese whey from the bulk of the water, lactose and dissolved salts. They do not indicate, however, that the constituent proteins of that protein fraction can be concentrated and separated by their apparatus, or that such a separation and concentration can be achieved by altering the pH at which the fluid is subjected to ultrafiltration.

Johnson et al., U.S. Pat. No. 3,431,201 relates to an improved hyperfiltration process for reducing the concentration of solute in an aqueous solution. The improvement comprises contacting an aqueous feed solution with a hydrous metal oxide ion exchange mass so that the ions which are deleterious to hydrous metal oxide membranes may be removed from the feed solution prior to hyperfiltration through that form of membrane. By removing the interfering ions, this process reportedly increases the useful life of the membrane, provides a method for controlling the pH of the feed solution, and provides a method for adding membrane-forming material to the membrane. Johnson et al. report that solute rejection by a hydrous zirconium oxide membrane during hyperfiltration can be increased by modifying the pH of the feed solution to increase the anion exchange properties of the dynamic membrane. Johnson et al. modify pH to separate molecules on the basis of charge. They do not contemplate, however, separating components on the basis of size, where the effective "permeability size" of a component is controlled by modifying the pH of the fluid.

DISCLOSURE OF THE INVENTION

There is disclosed a claim 1 which is a process for concentrating a protein from a fluid and enriching the protein with respect to concentrations of proteins having different sizes and/or isoelectric points, said process comprising:

(a) introducing a fluid to a first metallic oxide ultrafiltration membrane, wherein the metallic oxide is deposited on a rigid porous surface, at a pH which is below the isoelectric point of a selected protein, whereby a retentate containing the selected protein is produced;

(b) subjecting said retentate to a second ultrafiltration at a pH above the isoelectric point of the selected protein, whereby a permeate containing the selected protein is produced; and (c) collecting the permeate containing the selected protein.

There is also disclosed a claim 6 which is a process for concentrating a protein from a fluid and enriching the protein with respect to concentrations of proteins having a different size and isoelectric point, said process comprising:

(a) introducing a fluid to a first metallic oxide ultrafiltration membrane, wherein the metallic oxide is deposited on a rigid porous surface, at a pH which is above the isoelectric point of a selected protein whereby a permeate containing the selected protein is produced;

(b) subjecting said permeate to a second ultrafiltration at a pH below the isoelectric point of the protein, whereby a retentate containing the selected protein is produced; and (c) collecting then retentate containing the selected protein.

BRIEF SUMMARY

The present invention relates to an ultrafiltration process for enriching and concentrating a desired protein from a fluid containing various proteins by using metallic oxide ultrafiltration membranes and a pH shift. The process uses the same ultrafiltration membrane for two successive ultrafiltrations, shifting the pH between the two successive ultrafiltrations, in order to remove materials of lower molecular weight or higher molecular weight than the desired protein on the basis of charge, as well as size. A diafiltration of the fraction containing the desired protein can be performed to enrich the fraction so as to enhance the separation obtained by the second ultrafiltration. Additionally, a third ultrafiltration may be used at a pH different from the pH of the second ultrafiltration to further enrich the desired protein.

Metallic oxide is deposited on a rigid porous surface to form the metallic oxide ultrafiltration membrane, so that the membrane has an initial permeability (P) to water of from about 0.24 to about 3.6 as determined by the formula $$P = \frac{\text{Permeate Flux}}{\text{Inlet Pressure}}$$

where permeate flux is the number of liters of water passing through a square meter of membrane per hour and inlet pressure is measured in kiloPascals. A preferred initial membrane permeability to water is about 2.4.

During the filtering of a protein through an ultrafiltration membrane, the product which passes through the membrane is known as the ultrafiltrate or "permeate". The constituents which are held back or retained are known as the "retentate" or protein concentrate.

To fractionate a protein from the lower and higher molecular weight components in a fluid, the fluid is introduced to a first metallic oxide ultrafiltration membrane at an inlet pressure of from about 34.5 to about 12,420 kiloPascals, preferably from about 207 to about 276 kiloPascals, at a permeate flux of the rigid porous tube from about 25.5 to about 51 liters per square meter per hour, preferably at about 34 liters per square meter per hour, at a circulating fluid velocity greater than or equal to 4.5 meters per second, and at a pH which is below the isoelectric point of the protein to produce a retentate containing the protein, or at a pH which is above the isoelectric point of the protein to produce a permeate containing the protein. The term isoelectric point means the pH at which the net charge on a molecule in solution is zero.

If the retentate of the first ultrafiltration contains the protein, this retentate containing the protein may be submitted to diafiltration with an aqueous solution at constant volume or added incrementally, the volume of the aqueous solution used for the diafiltration generally being from about 5% to about 100% of the initial protein solution volume to produce a diafiltered retentate. Physiological saline solution and 5% sucrose solution are among the preferred aqueous solutions to be used for diafiltration, as well as water. If diafiltration is not desired, this retentate containing the protein is subjected to a second ultrafiltration at the parameters of the first ultrafiltration except that the pH is adjusted to be above the isoelectric point of the desired protein, whereby a permeate containing the protein is produced. This permeate containing the protein is then collected.

If the permeate of the first ultrafiltration contains the protein, this permeate containing the protein is subjected to a second ultrafiltration at the parameters of the first ultrafiltration except that the pH is below the isoelectric point of the desired protein, whereby a retentate containing the protein is produced. This retentate containing the protein may be submitted to diafiltration with an aqueous solution at constant volume or in batches, the volume of the aqueous solution used for the diafiltration generally being from about 5% to about 100% of the initial protein solution volume to produce a diafiltered retentate. Physiological saline solution and 5% sucrose solution are among the preferred aqueous solutions to be used for diafiltration, as well as water. This retentate containing the protein is then collected. If diafiltration is not desired, the retentate containing the protein is collected directly.

Further aspects and advantages of the invention will be apparent to those skilled in the art upon review of the following detailed description taken in conjunction with the FIGS. and the appended claims.

BRIEF DESCRIPTION OF THE FIGURES

FIG. 6 is a HPLC which shows the protein profile of the original egg yolk feed;

DETAILED DESCRIPTION OF THE INVENTION

The present invention provides a process for obtaining a specific protein-enriched product by ultrafiltering a fluid through metallic membranes and using a pH shift to fractionate components of lower molecular weight or higher molecular weight than the desired protein on the basis of charge as well as size. The process of the present invention makes feasible the fractionation of immunoglobulins, particularly IgG, from the majority of the other proteins contained in milk, cheese whey or other immunoglobulin containing fluids and involves two factors: (1) the metallic membrane produces a high rejection of IgG at a pH of 5.8 or lower, but a much lower rejection of IgG at a pH of 6.5 or greater, and (2) the metallic membrane allows continual passage of smaller molecular weight proteins at any pH level, even at very high concentrations.

Figure 1:
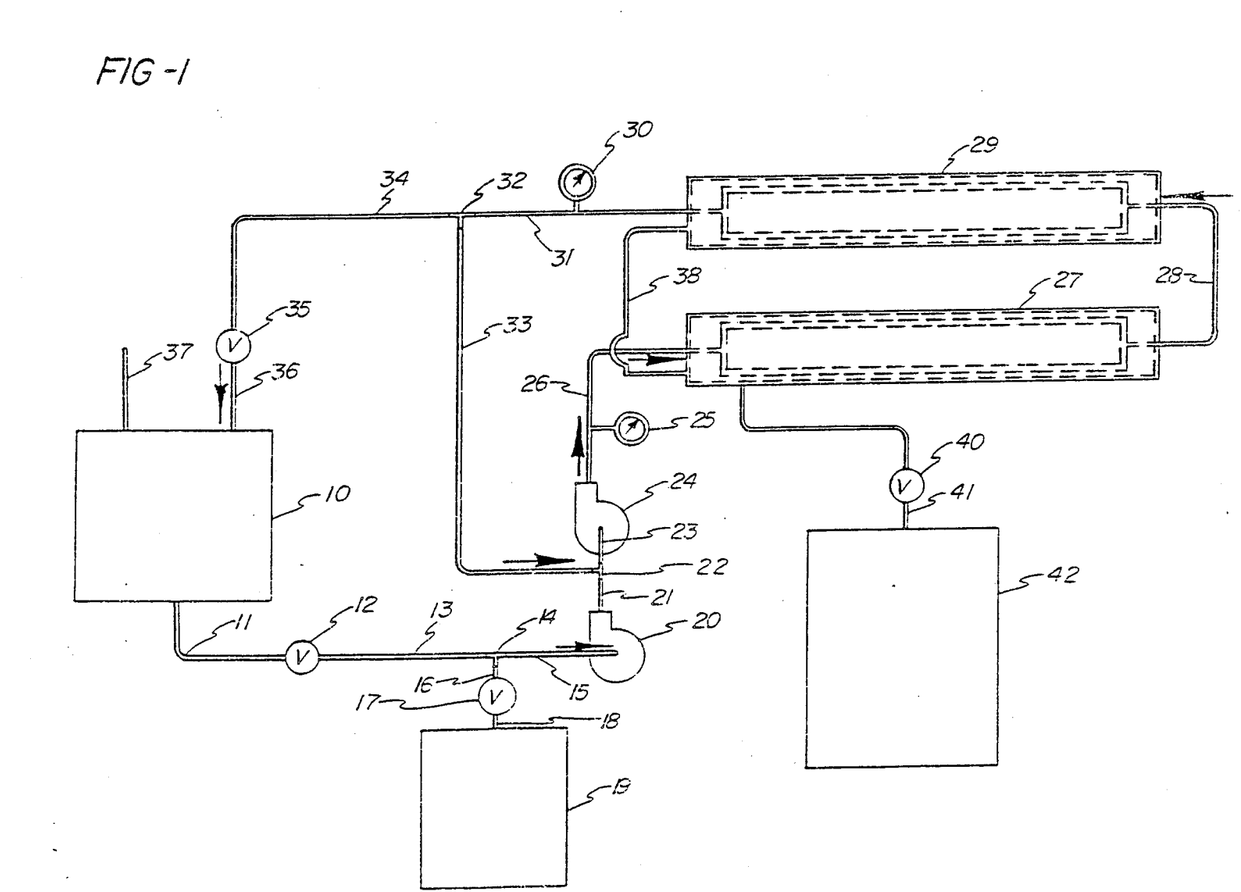
FIG. 1 is a schematic diagram of an exemplary apparatus useful in the practice of the instant invention.

FIG. 1 is a schematic diagram of an exemplary apparatus according to the present invention. An output from a reservoir 10 is connected to an input of a control valve 12 by a line 11. An output from the control valve 12 is connected to an input of a T connection 14 by a line 13. An output from the T connection 14 is connected to an input of a control valve 17 by a line 16. An output from the control valve 17 is connected to an input of a retentate collection reservoir 19 by a line 18. An output from the T connection 14 is connected to an input of a pump 20 by a line 15. An output from the pump 20 is connected to an input of a T connection 22 by a line 21. An output of the T connection 22 is connected to a pump 24 by a line 23. An output from the pump 24 is connected to an input of a module 27 by a line 26. A pressure gauge 25 is attached to the line 26. A retentate output from the module 27 is connected to an input of a module 29 by a line 28. A retentate output from the module 29 is connected to a T connection 32 by a line 31. A pressure gauge 30 is attached to the line 31. An output of the T connection 32 is connected to an input of a control valve 35 by a line 34. An output of the T connection 32 is connected to an input of the T connection 22 by a line 33. An output from the control valve 35 is connected to an input of the reservoir 10 by a line 36. An addition of a fluid to the reservoir 10 is controlled by an entry port 37. A permeate output from module 29 is connected to the outer shell of module 27 by a line 38. A permeate output from the module 27 is connected to an input of a control valve 40 by a line 39. An output from the control valve 40 is connected to a permeate collection reservoir 42 by a line 41.

The fluid containing the protein which is to be enriched and concentrated is added to the reservoir 10 through the entry port 37. In general, the fluid is acidified to a pH suitably below the isoelectric point of the protein by the addition of any food grade acid, for example, phosphoric or acetic acid through the entry port 37. After the acidification, the fluid is pumped out of the reservoir 10 through the line 11, control valve 12 and lines 13 and 15 by the pump 20, which is a diaphragm positive displacement pump. Pump 20 creates the inlet pressure for the ultrafiltration. The fluid exits the pump 20 by the line 21, passes through the line 23, and enters the pump 24 which is a C-114 centrifugal pump. The pump 24 propels the fluid into the ultrafiltration modules 27 and 29 by means of the line 26. The inlet pressure of the fluid is measured by the pressure gauge 25. The ultrafiltration modules 27 and 29, which are connected by the line 28, separate the fluid into a retentate and a permeate. The permeate from the module 29 flows to the outer shell of module 27 through the permeate line 38. The permeate is drained from module 27 by means of line 39 through control valve 40 into the permeate collection reservoir 42. The retentate exits the module 29 through the line 31. The outlet pressure is measured by the pressure guage 30. A portion of the retentate is recirculated directly back to the ultrafiltration modules by the line 33. The remainder of the retentate flows through the line 34, past the concentrate control valve 35 into the reservoir 10 to be recirculated again until the desired concentration of the retentate is achieved. After concentration, the retentate flows from the reservoir through the line 11, past the control valve 12, through line 13 to a T connection 14. The retentate flows through this T connection to line 16, through control valve 17 and then into the retentate collection reservoir 19.

The following example is directed to a specific embodiment of the present invention and is not to be construed as limiting the scope of the invention.

EXAMPLE 1

The protein concentrations and protein ratios (with IgG as the basis) of a chedder cheese whey starting material obtained from a cheese manufacturing plant are presented in Table 1.

TABLE 1

| Protein | Conc. (mg/ml) | Ratio |
| --- | --- | --- |
| IgG | 0.29 | 1.0 |
| BSA | 0.25 | 0.9 |
| beta-lactoglobulin | 2.58 | 9.0 |
| alpha-lactalbumin | 0.69 | 2.4 |

Figure 2:
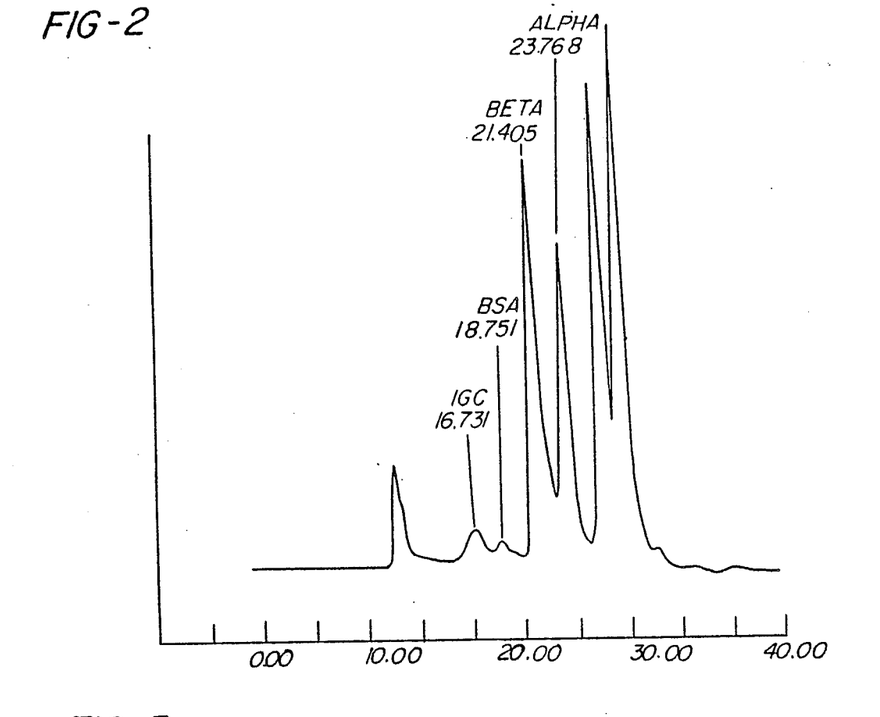
FIG. 2 is a High Pressure Liquid Chromatogram (HPLC) which shows the protein profile of the original whey feed.
Figure 3:
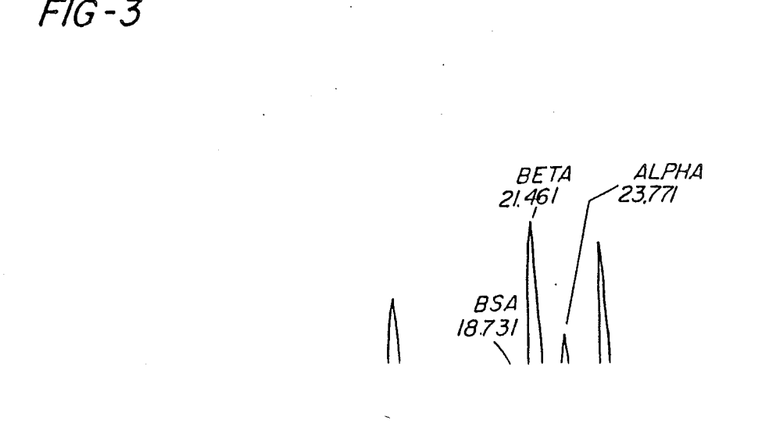
FIG. 3 is a HPLC which shows the protein profile of the retentate of the whey feed after a 15-fold concentration by ultrafiltration at pH 5.0.

FIG. 2 shows the HPLC profile of the whey starting material. The pH of the whey was adjusted to 5.0 by addition of food grade acid and 94.5 kg of the whey was concentrated 15-fold by passing the whey through a CARRE BIO-1 CI-200 membrane, available from CARRE, Inc., Seneca, S.C., with an initial permeability to water of 2.5 at 36.7° C. The permeate flux was 50.9 1/m²/hr initially and was 34 1/m²/hr after the 15-fold concentration. The inlet pressure was 207 kP and the circulating velocity of the fluid was 6.1 m/s. FIG. 3 shows the HPLC profile of the whey after the 15-fold concentration. The protein concentrations and ratios after the 15-fold concentration are provided in Table 2.

TABLE 2

| Protein | Conc.(mg/ml) | Ratio |
| --- | --- | --- |
| IgG | 4.65 | 1.0 |
| BSA | 4.05 | 0.9 |
| beta-lactoglobulin | 23.72 | 5.1 |
| alpha-lactalbumin | 4.35 | 0.9 |

The first concentration significantly improved the protein ratios in favor of IgG with close to 100% recovery of the IgG into the retentate. The IgG to beta-lactoglobulin ratio shifted from 1:9.0 to 1:5.1. The profile also showed a near elimination of peptides and a very large reduction in the proportion of alphalactalbumin to IgG.

Further enrichment of the IgG was next accomplished by diafiltration of the concentrate at pH 5.0 with water in the amount of one-fifth the weight of the original whey or 18.9 kg of water through the CARRE BIO-1 CI-200 membrane with all the parameters being kept the same. The protein concentrations and ratios after diafiltration and dilution to a 2.2 fold concentration compared to the original whey are shown in Table 3.

TABLE 3

| Protein | Conc. (mg/ml) | Ratio |
| --- | --- | --- |
| IgG | 0.61 | 1.0 |
| BSA | 0.53 | 0.9 |
| beta-lactoglobulin | 1.99 | 3.2 |
| alpha-lactalbumin | 0.27 | 0.4 |

Figure 4:
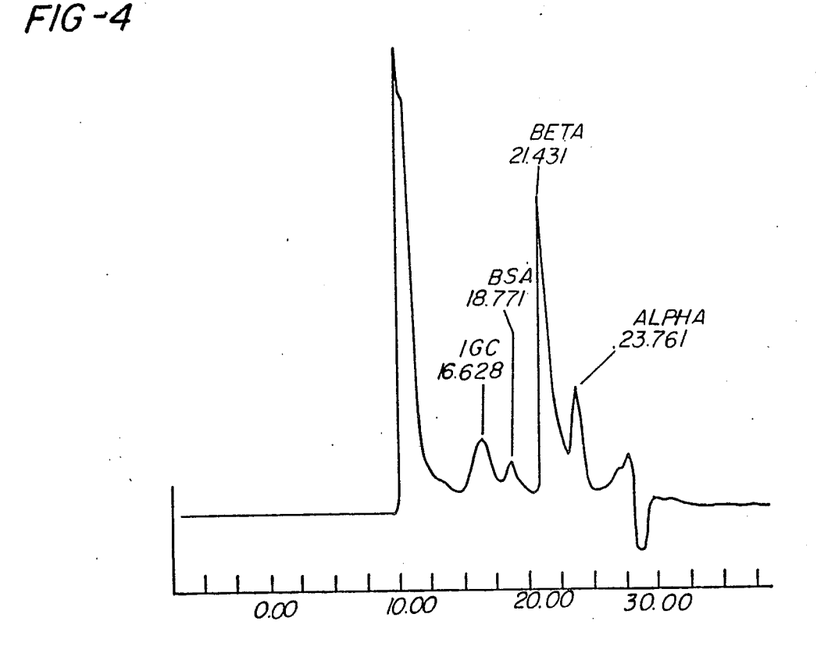
FIG. 4 is a HPLC which shows the protein profile of the retentate of the whey feed after diafiltration with a volume of water equal to one-fifth the initial whey volume.

The HPLC of FIG. 4 shows that after diafiltration the IgG concentration represented 96% recovery of the total IgG from the starting whey (i.e., 0.61 mg/ml divided by 2.2 equals a concentration of 0.28 mg/ml). There was a large increase in the void volume peak from FIG. 2 to FIG. 4 because the compounds of larger molecular weight than IgG were being concentrated as well.

Removal of the larger molecular weight compounds remaining after the fractionation of IgG from the other whey proteins was accomplished by adjusting the pH of the whey concentrate to 7.0 by addition of food grade base, such as NaOH, and passing it through the same CARRE BIO-1 CI-200 membrane used in the initial step, at all the same parameters, after cleaning the tubes with, for example, an alkaline hypochlorite solution at pH 11 followed by a nitric/phosphoric acid solution at pH 2 and a water rinse. This ultrafiltration removed large particulate matter, such as casein micelles, fat globules and bacteria, but passed 90% of the IgG into the permeate. The resulting permeate was a water-clear, near sterile solution enriched in IgG. The protein concentrations and ratios of the second permeate are shown in Table 4.

TABLE 4

| Protein | Conc. (mg/ml) | Ratio |
| --- | --- | --- |
| IgG | 0.26 | 1.0 |
| BSA | 0.19 | 0.7 |
| beta-lactoglobulin | 1.17 | 4.5 |
| alpha-lactalbumin | 0.20 | 0.7 |

Figure 5:
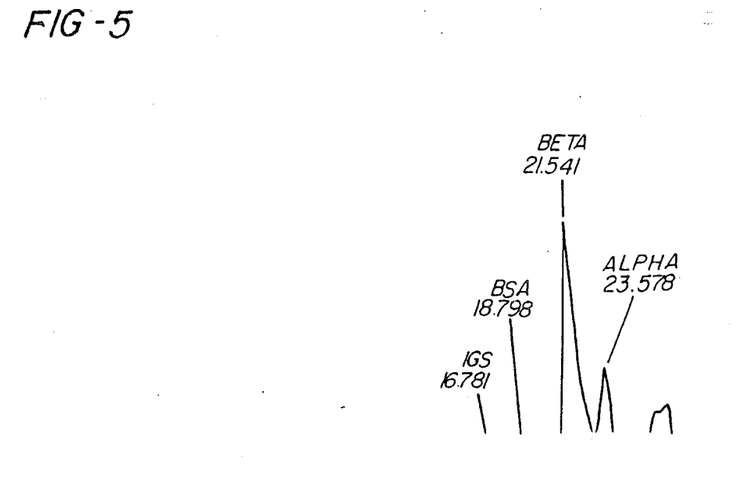
FIG. 5 is a HPLC which shows the protein profile of the permeate of the whey feed after ultrafiltration at pH 7.0.

FIG. 5 shows the HPLC profile of the final permeate. The bacterial cell population was reduced by 7.3 logs, enabling the solution to be easily and efficiently polished with standard bacterial filters for a final sterile product.

Figure 8:
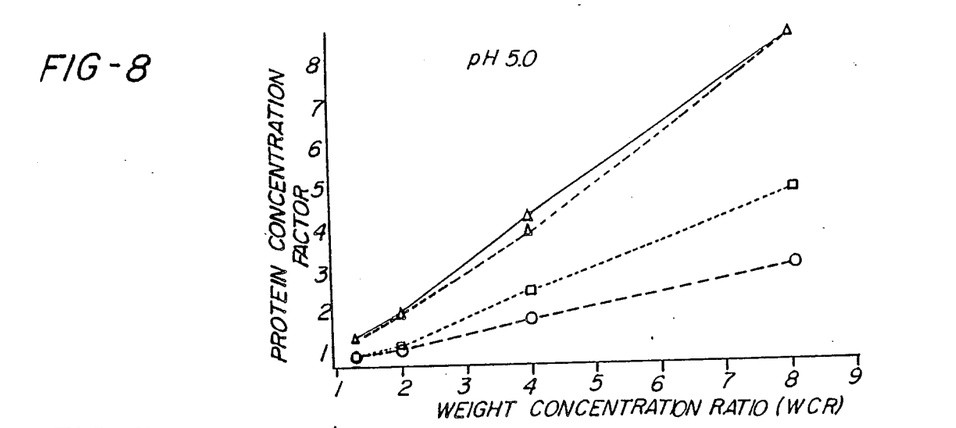
FIG. 8 is a graph which shows the protein concentration factor of four proteins in whey (immunoglobulin, bovine serum albumin, beta-lactoglobulin and alpha-lactalbumin) versus the weight concentration ratio at pH 5.0.
Figure 9:
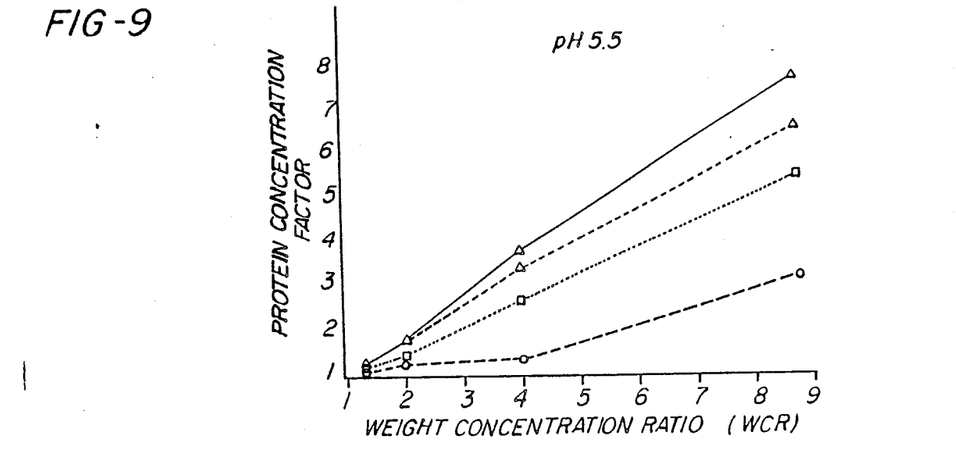
FIG. 9 is a graph which shows the protein concentration factor of four proteins in whey (immunoglobulin, bovine serum albumin, beta-lactoglobulin and alpha-lactalbumin) versus the weight concentration ratio at pH 5.5.
Figure 10:
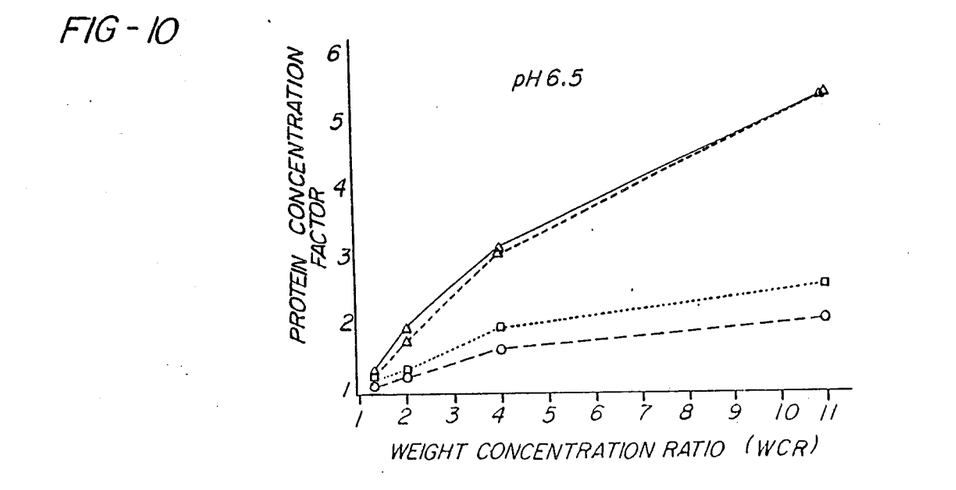
FIG. 10 is a graph which shows the protein concentration factor of four proteins in whey (immunoglobulin, bovine serum albumin, beta-lactoglobulin and alpha-lactalbumin) versus the weight concentration ratio at pH 6.5.

The weight concentration ratio (WCR) is a method of calculating yield. It is determined by calculating the ratio of the weight of the starting material to the weight of the material after a single pass through the ultrafiltration membrane. Protein concentration factor (PCF) is calculated by determining the concentration of a particular protein and dividing that figure by the original concentration of that protein in the feed whey. 100% retention of a protein is obtained when the protein concentration factor equals the weight concentration ratio. FIGS. 8, 9, and 10 are graphs which show the protein concentration factors of 4 proteins in whey (PCF values) versus the weight concentration ratio (WCR values) at various pH's. Alpha-lactalbumin is represented by circles; beta-lactoglobulin is represented by squares; bovine serum albumin (BSA) is represented by diamonds; and IgG is represented by triangles.

Analysis of FIGS. 8 and 10 indicates that at pH 5.0 and pH 6.5, respectively, IgG and BSA have the same PCF value. This illustrates that at these pH values, IgG cannot be separated from BSA in a single pass through the ultrafiltration method disclosed by the present invention. Analysis of FIG. 9 indicates that at pH 5.5, however, IgG has a PCF equal to about 7.5 whereas BSA has a PCF equal to about 6.5. This illustrates that IgG can be separated from BSA in a single pass through the ultrafiltration method disclosed by the present invention at pH=5.5.

It is important in any membrane process to clean the membranes back to their original permeability to water so as to maintain maximum performance with respect to permeate flux. In the process described herein, the cleaning is equally important for maintaining separation capabilities. This is due in large part to the dependence on charge for separations.

Both organic foulants, which are primarily proteins, and mineral foulants abound in milk and whey and can significantly alter membrane permeability. The operational parameters of high velocity and low pressure minimize protein fouling as evidenced by steady fluxes and continued protein passage, even at very high volume recoveries or concentrations. However, separations could suffer if the membranes were not properly cleaned.

Acid washing has been found to maintain separation capability as well as recovering membrane permeability. A preferred commercial cleaning fluid is URACIL 75, available from the Henkel Corp., Burlington, Iowa. This acid cleaner is to be exposed to the membrane at the operating parameters of the ultrafiltration membrane. Another significant cleaning procedure is the use of back flow during both base and acid cleaning. In cleaning studies, the use of back flow during both acid and base cleaning after a typical whey run was found to increase permeability to water between 8 and 69 per cent. In other cleaning studies, back flow gave immediate improvement in water permeability even after several previous cycles of base/acid cleaning without backflow. Therefore, it is recommended that backflow be used in both base and acid cleaning steps.

EXAMPLE 2

Figure 7:
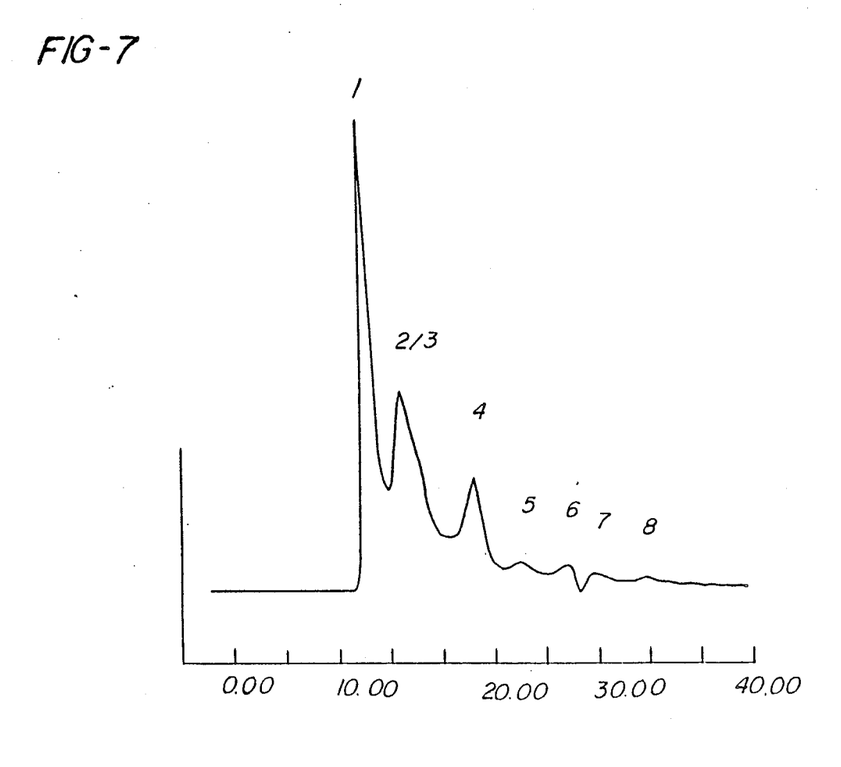
FIG. 7 is a HPLC which shows the protein profile of the retentate of the egg yolk feed after a 10-fold concentration by ultrafiltration at pH 5.0.

Egg yolks were diluted with water to obtain a solution containing 5% yolk as compared to water on a weight to weight basis. FIG. 6 shows the HPLC profile of the egg yolk starting material. Peak 3 was identified as IgG based on retention time. Peak 2 may also be IgG because peaks 2 and 3 were not well separated. The pH of the solution was adjusted to 5.0 by addition of phosphoric acid and 75.5 liters of this solution was concentrated 10-fold by passing the egg yolk solution through the CARRE CI-200 membrane with an initial permeability to water of 2.5 at 36.7° C. The permeate flux was 50.9 $1/m^2/Hr$ at 37.8° C. The inlet pressure was 207 kP and the circulating velocity of the fluid was 6.1 m/s. FIG. 7 shows the HPLC profile of the egg yolk solution after the 10-fold concentration. Peaks 1, 2, and 3 increased in proporation to peaks 4–8, indicating that IgG was concentrated, whereas smaller molecular weight proteins were drastically reduced in concentration. This example suggests that other fluids can be concentrated and enriched by the process disclosed by the present invention.

EXAMPLE 3

Blood serum was diluted with water to obtain a 2X dilution. The pH of the solution was adjusted to 5.0 by addition of phosphoric acid and 75.5 liters of this solution was concentrated 20-fold by passing the blood serum solution through the CARRE CI-200 membrane with an initial permeability to water of 2.5 at 36.7° C. The permeate flux was 30.5 at 32.2° C, the inlet pressure was 207 kP and the circulating velocity of the fluid was 6.1 m/s. Although BSA was not separated from IgG using the ultrafiltration apparatus described above, at pH 7.0 some fractionation of IgG and BSA was observed. Additionally, the results depicted in FIGS. 8, 9, and 10 illustrate that separation of BSA and IgG may be obtained by ultrafiltration at a pH of 5.5.

The ultrafiltration system that has been found to provide the surprising results noted above is generally described in U.S. Pat. No. 4,200,533 to Gaddis et al and more specifically described in U.S. Pat. No. 4,762,619 to Gaddis et al. Certain particular parameters of the system per se, for purposes of the present invention, are not particularly set forth therein. Particularly, according to the present invention, the support upon which the food grade titanium dioxide is deposited is preferably a rigid porous surface, such as sintered stainless steel, so as to alleviate any concern for certain process conditions, such as temperature and pressure which might otherwise normally adversely affect the support or not be suitable at all therefor, or for certain cleaning conditions, such as acid or base washing. The titanium dioxide coated CI-200 membrane and the BIO-1 CI-200 membrane used in the present invention are available from Carre, Inc., Seneca, S.C. A modified BIO-1 CI-200 membrane which has not yet been tested may also prove useful in the enrichment and concentration of a selected protein from other proteins in a solution. Future modifications of this membrane, as available from CARRE, are intended to be within the scope of the present invention. It is expected that a rigid porous surface made of ceramic materials also could serve as a support for the food grade metallic oxide membrane.

It is anticipated and expected that proteins from other biological fluids than those described above, such as skim milk, whole milk, colostrum, colostral whey, whole blood, tissue culture fluids, or fermentation broths may be enriched and concentrated by employing the method of the present invention. The foregoing detailed description is given for clearness of understanding only, and no unnecessary limitations should be understood therefrom, as aspects and advantages within the scope of the present invention will be apparent to those skilled in the art.

We claim:

1. A process for concentrating a protein from a fluid and enriching the protein with respect to concentrations of proteins having different sizes and/or isoelectric points, said process comprising:
   (a) introducing a fluid to a first metallic oxide ultrafiltration membrane, at a pH which is below the isoelectric point of a selected protein, whereby a retentate containing the selected protein is produced.
   (b) subjecting said retentate to a second ultrafiltration at a pH above the isoelectric point of the selected protein, whereby a permeate containing the selected protein is produced; and
   (c) collecting the permeate containing the selected protein.

2. The process as recited in claim 1, wherein said introducing step comprises the step of exposing the fluid to a metallic oxide ultrafiltration membrane at an initial permeability to water of from about 0.24 to about 3.6, at an inlet pressure of from about 34.5 to about 12,420 kiloPascals, at a permeate flux of from about 25.5 to about 51 liters per square meter per hour, and at a circulating fluid velocity greater than or equal to 4.5 meters per second and wherein said subjecting step comprises the step of filtering the fluid through a metallic oxide ultrafiltration membrane at an initial permeability to water of from about 0.24 to about 3.6, at an inlet pressure of from about 34.5 to about 12,420 kiloPascals, at a permeate flux of from about 25.5 to about 51 liters per square meter per hour, and at a circulating fluid velocity greater than or equal to 4.5 meters per second.

3. The process as recited in claim 1, further comprising the step of submitting said retentate containing the selected protein to a diafiltration with an aqueous solution.

4. The process as recited in claim 3, wherein said submitting step comprises the step of exposing the retentate containing the selected protein to a diafiltration with an aqueous solution at the parameters of said first ultrafiltration, the volume of the aqueous solution used for the diafiltration being from about 5% to about 100% of the initial protein solution volume.

5. The process as recited in claim 4, wherein said exposing step comprises the step of employing a volume used for said diafiltration of from about one-fifth to about one-third the initial protein solution volume.

6. A process for concentrating a protein from a fluid and enriching the protein with respect to concentrations of proteins having different sizes and/or isoelectric points, said process comprising:
   (a) introducing a fluid to a first metallic oxide ultrafiltration membrane, at a pH which is above the isoelectric point of a selected protein, whereby a permeate containing the selected protein is produced;
   (b) subjecting said permeate to a second ultrafiltration at a pH below the isoelectric point of the protein, whereby a retentate containing the selected protein is produced; and
   (c) collecting the retentate containing the selected protein.

7. The process as recited in claim 6, wherein said introducing step comprises the step of exposing the fluid to a metallic oxide ultrafiltration membrane at an initial permeability to water of from about 0.24 to about 3.6, at an inlet pressure of from about 34.5 to about 12,420 kiloPascals, at a permeate flux of from about 25.5 to about 51 liters per square meter per hour, and at a circulating fluid velocity greater than or equal to 4.5 meters per second and wherein said subjecting step comprises the step of filtering the fluid through a metallic oxide ultrafiltration membrane at an initial permeability to water of from about 0.24 to about 3.6, at an inlet pressure of from about 34.5 to about 12,420 kiloPascals, at a permeate flux of from about 25.5 to about 51 liters per square meter per hour, and at a circulating fluid velocity greater than or equal to 4.5 meters per second.

8. The process as recited in claim 6, further comprising the step of submitting said retentate containing the selected protein to a diafiltration with an aqueous solution.

9. The process as recited in claim 8, wherein said submitting step comprises the step of exposing the retentate containing the selected protein to diafiltration with an aqueous solution at the parameters of said first ultrafiltration, the volume of the aqueous solution used for the diafiltration being from about 5% to about 100% of the initial protein solution volume.

10. The process as recited in claim 9, wherein said exposing step comprises the step of employing a volume used for said diafiltration of from about one-fifth to about one-third the initial protein solution volume.

11. A process for concentrating an immunoglobulin from a fluid and enriching the immunoglobulin with respect to concentrations of proteins having different sizes and/or isoelectric points, said process comprising:
   (a) introducing a fluid to a first metallic oxide ultrafiltration membrane, at a pH which is below the isoelectric point of an immunoglobulin, whereby a retentate containing the immunoglobulin is produced;
   (b) subjecting said retentate to a second ultrafiltration at a pH above the isoelectric point of the immunoglobulin, whereby a permeate containing the immunoglobulin is produced; and
   (c) collecting the permeate containing the immunoglobulin.

12. The process as recited in claim 11, wherein said introducing step comprises the step of exposing the fluid to a metallic oxide ultrafiltration membrane at an initial permeability to water of from about 0.24 to about 3.6, at an inlet pressure of from about 34.5 to about 12,240 kiloPascals at a permeate flux of from about 25.5 to about 51 liters per square meter per hour, and at a circulating fluid velocity greater than or equal to 4.5 meters per second and wherein said subjecting step comprises the step of filtering the fluid through a metallic oxide ultrafiltration membrane at an initial permeability to water of from about 0.24 to about 3.6, at an inlet pressure of from about 34.5 to about 12,420 kilopascals, at a permeate flux of from about 25.5 to about 51 liters per square meter per hour, and at a circulating fluid velocity greater than or equal to 4.5 meters per second.

13. The process as recited in claim 11, further comprising the step of submitting said retentate containing the immunoglobulin to a diafiltration with an aqueous solution.

14. The process as recited in claim 13, wherein said submitting step comprises the step of exposing the retentate containing the immunoglobulin to diafiltration with an aqueous solution at the parameters of said first ultrafiltration, the volume of the aqueous solution used for the diafiltration being from about 5% to about 100% of the initial protein solution volume.

15. The process as recited in claim 14, wherein said exposing step comprises the step of employing a volume used for said diafiltration of from about one-fifth to about one-third the initial fluid volume.

16. The process as recited in claim 11, wherein the initial permeability to water of said introducing and subjecting steps is about 2.4.

17. The process as recited in claim 11, wherein said introducing and subjecting steps are carried out at an inlet pressure of from about 207 to about 276 kiloPascals.

18. The process as recited in claim 11, wherein said introducing and subjecting steps are carried out at a permeate flux of about 34 liters per square meter per hour.

19. The process as recited in claim 11, wherein said introducing step is carried out at a pH=5.5.

20. The process as recited in claim 11, wherein said subjecting step is carried out at a pH=7.

21. The process as recited in claim 11 wherein said introducing and subjecting steps are carried out at a temperature of from about 15° C. to about 55° C.

22. A process for concentrating an immunoglobulin from a fluid and enriching the immunoglobulin with respect to concentrations of proteins having different sizes and/or isoelectric points, said process comprising:
(a) introducing a fluid to a first metallic oxide ultrafiltration membrane, at a pH which is above the isoelectric point of an immunoglobulin, whereby a permeate containing the immunoglobulin is produced;
(b) subjecting said permeate to a second ultrafiltration at a pH below the isoelectric point of the immunoglobulin, whereby a retentate containing the immunoglobulin is produced; and
(c) collecting the retentate containing the immunoglobulin.

23. The process as recited in claim 22, wherein said introducing step comprises the step of exposing the fluid to a metallic oxide ultrafiltration membrane at an initial permeability to water of from about 0.24 to about 3.6, at an inlet pressure of from about 34.5 to about 12,420 kiloPascals. at a permeate flux of from about 25.5 to about 51 liters per square meter per hour, and at a circulating fluid velocity greater than or equal to 4.5 meters per second and wherein said subjecting step comprises the step of filtering the fluid through a metallic oxide ultrafiltration membrane at an initial permeability to water of from about 0.24 to about 3.6, at an inlet pressure of from about 34.5 to about 12,420 kiloPascals, at a permeate flux of from about 25.5 to about 51 liters per square meter per hour, and at a circulating fluid velocity greater than or equal to 4.5 meters per second.

24. The process as recited in claim 22, further comprising the step of submitting said retentate containing the immunoglobulin to a diafiltration with an aqueous solution.

25. The process as recited in claim 24, wherein said submitting step comprises the step of exposing the retentate containing the immunoglobulin to diafiltration with an aqueous solution at the parameters of said first ultrafiltration, the volume of the aqueous solution used for the diafiltration being from about 5% to about 100% of the initial protein solution volume.

26. The process as recited in claim 25, wherein said exposing step comprises the step of employing a volume used for said diafiltration of from about one-fifth to about one-third the initial fluid volume.

27. The process as recited in claim 22, wherein said introducing and subjecting steps are carried out at an initial permeability to water of about 2.4.

28. The process as recited in claim 22, wherein said introducing and subjecting steps are carried out at an inlet pressure of from about 207 to about 276 kiloPascals.

29. The process as recited in claim 22, wherein said introducing and subjecting steps are carried out at a permeate flux of about 34 liters per square meter per hour.

30. The process as recited in claim 22, wherein said introducing step is carried out at a pH=7.

31. The process as recited in claim 22, wherein said subjecting step is carried out at a pH=5.5.

32. The process as recited in claim 22, wherein said introducing and subjecting steps are carried out at a temperature of from about 15° C. to about 55° C.

33. The process as recited in claim 1, wherein the rigid porous surface has a pore size before deposition of the metallic oxide of from about 2 to about 5 microns.

34. The process as recited in claim 6, wherein the rigid porous surface has a pore size before deposition of the metallic oxide of from about 2 to about 5 microns.

35. The process as recited in claim 11, wherein the rigid porous surface has a pore size before deposition of the ultrafiltration membrane of from about 2 to about 5 microns.

36. The process as recited in claim 22, wherein the rigid porous surface has a pore size before deposition of the ultrafiltration membrane of from about 2 to about 5 microns.

37. The process as recited in claim 11, wherein the fluid is selected from one of the following:
whey from milk acidified by fermentation or by direct acid precipitation of casein, skim milk, whole milk, egg yolk, blood serum, colostrum, colostral whey, whole blood, tissue culture fluid containing immunoglobulin or fermentation broth containing immunoglobulin.

38. The process as recited in claim 22, wherein the fluid is selected from one of the following:
whey from milk acidified by fermentation or by direct acid precipitation of casein, skim milk, whole milk, egg yolk, blood serum, colostrum, colostral whey, whole blood, tissue culture fluid containing immunoglobulin or fermentation broth containing immunoglobulin.

39. A process for concentrating an immunoglobulin from whey and enriching the immunoglobulin with respect to concentrations of other proteins having a different size and isoelectric point, said process comprising:
(a) introducing a whey feed to a first metallic oxide ultrafiltration membrane, wherein the metallic oxide is deposited on a rigid porous surface, at a pH of 5.0, which is below the isoelectric point of an immunoglobulin, whereby a first retentate containing the immunoglobulin is produced;
(b) submitting said first retentate to an ultrafiltration diafiltration with water at constant volume, at the parameters of said first ultrafiltration, the volume of water used for the diafiltration being about one-fifth the initial protein solution volume;

(c) subjecting said first retentate to a second ultrafiltration at the parameters of said first ultrafiltration except that the pH is equal to 7.0, whereby a permeate containing the immunoglobulin is produced; and (d) collecting the permeate containing the immunoglobulin.

40. The process as recited in claim 39, wherein said introducing step comprises the step of exposing the whey to a metallic oxide ultrafiltration membrane at an initial permeability to water of 2.5, at an inlet pressure of 207 kP, at a permeate flux of 50.9 to 34 $1/m^2/Hr$, and at a circulating fluid velocity of 6.1 m/s.

* * * * *

UNITED STATES PATENT AND TRADEMARK OFFICE
CERTIFICATE OF CORRECTION

PATENT NO. :  4,897,465

DATED     :  Jan. 30, 1990

INVENTOR(S) :  Christopher T. Cordle, Larry G. Criswell, and Ronald L. Thomas

It is certified that error appears in the above-identified patent and that said Letters Patent is hereby corrected as shown below:

In Abstract, line 3:
Change from:  tein conaining fluids.  Illustratively, IgG is concentrated
      to:    tein containing fluids.  Illustratively, IgG is concentrated Column 11, line 17:

Change from:  tate containing the selected protein is produced.
      to:    tate containing the selected protein is produced;

Figs. 2, 3, 4 and 5 should be deleted to appear as per attached Figs.

FIG-2:
Change from:  IGC 16.731
      to:    IGG 16.731

FIG-3:
Completion of FIG-3 - Copy attached.

FIG-4:
Change from:  IGC 16.62
      to:    IGG 16.62

Signed and Sealed this

Thirteenth Day of August, 1991

*Attest:*

HARRY F. MANBECK, JR.

*Attesting Officer*        *Commissioner of Patents and Trademarks*

UNITED STATES PATENT AND TRADEMARK OFFICE
CERTIFICATE OF CORRECTION

PATENT NO. : 4,897,465

DATED : January 30, 1990

INVENTOR(S) : Christopher T. Cordle, et al

It is certified that error appears in the above-identified patent and that said Letters Patent is hereby corrected as shown below:

Fig. 5:

Change from" IGS 16781
      to:   IGG 16781
Completion of Fig-5    Copy attached.